United States Patent [19]
McCormick et al.

[11] Patent Number: 6,010,484
[45] Date of Patent: Jan. 4, 2000

[54] COMBINATION ENDOTRACHEAL AND INTRAOSSEOUS TRANSFUSION APPARATUS HOLDER

[76] Inventors: David A. McCormick, 9880 E. Palermo, Gold Canyon, Ariz. 85219; James I. Morgan, Jr., 8047 Recker Rd., Higley, Ariz. 85236

[21] Appl. No.: 09/004,047

[22] Filed: Jan. 7, 1998

[51] Int. Cl.$^7$ .................................................. A61M 16/00
[52] U.S. Cl. ................... 604/174; 128/DIG. 26
[58] Field of Search .................... 604/174, 179, 604/178; 128/DIG. 26

[56] References Cited

U.S. PATENT DOCUMENTS

| | | |
|---|---|---|
| 4,683,882 | 8/1987 | Laird . |
| 4,744,358 | 5/1988 | McGinnis . |
| 4,832,019 | 5/1989 | Weinstein et al. . |
| 4,867,154 | 9/1989 | Potter et al. . |
| 5,009,227 | 4/1991 | Nieuwstad . |
| 5,402,776 | 4/1995 | Islava . |

*Primary Examiner*—John D. Yasko
*Attorney, Agent, or Firm*—Parsons & Goltry; Michael W. Goltry; Robert A. Parsons

[57] ABSTRACT

An apparatus for holding an orally routed apparatus and for holding a flanged end of a body, the apparatus comprising a base including a channel, a bite block detachably engagable with the base and having a channel substantially alignable with the channel of the base, with the bite block engaged with the base defining a first configuration of the apparatus, the channel of the base and the channel of the bite block to substantially align and receive the orally routed apparatus, with the bite block detached from the base defining a second configuration of the apparatus, the channel of the base to receive a body having a flanged end with portions of the flanged end to overly and engage portions of the base, and an engagement assembly for securing the orally routed apparatus and the body with the base in the first and second configurations, respectively.

17 Claims, 5 Drawing Sheets

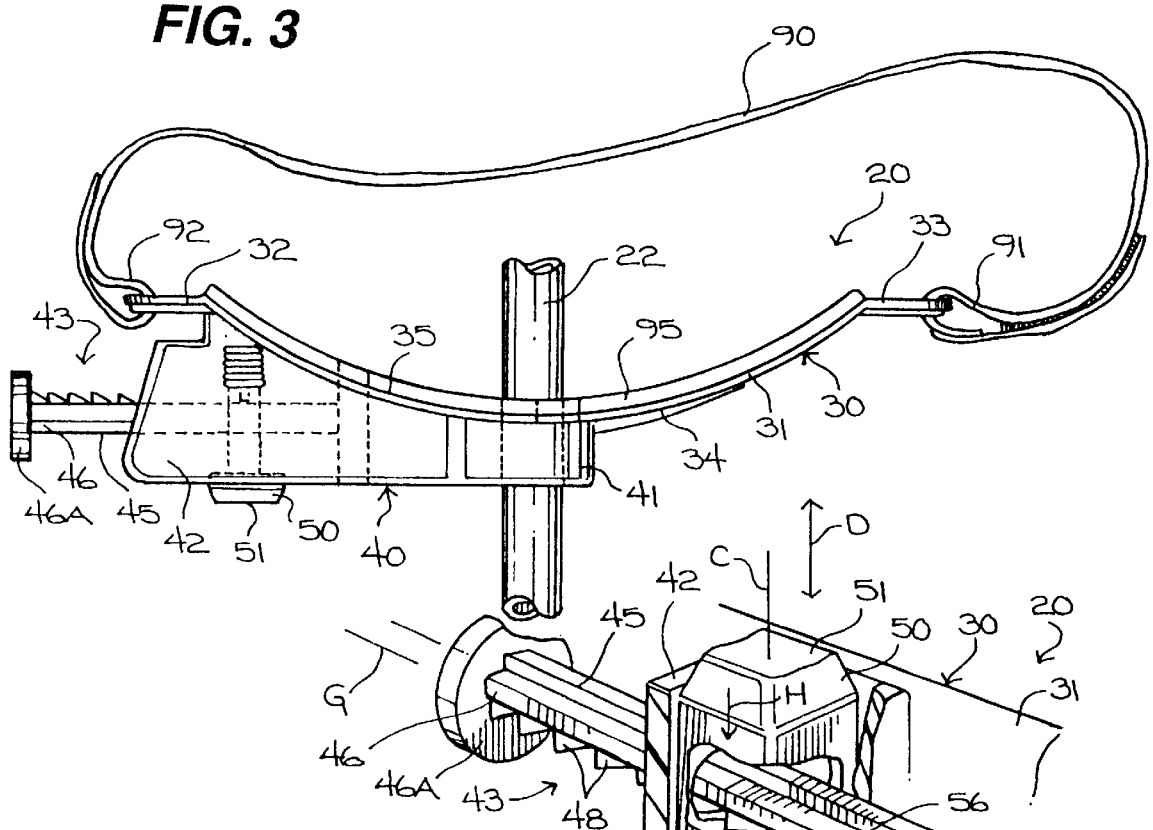
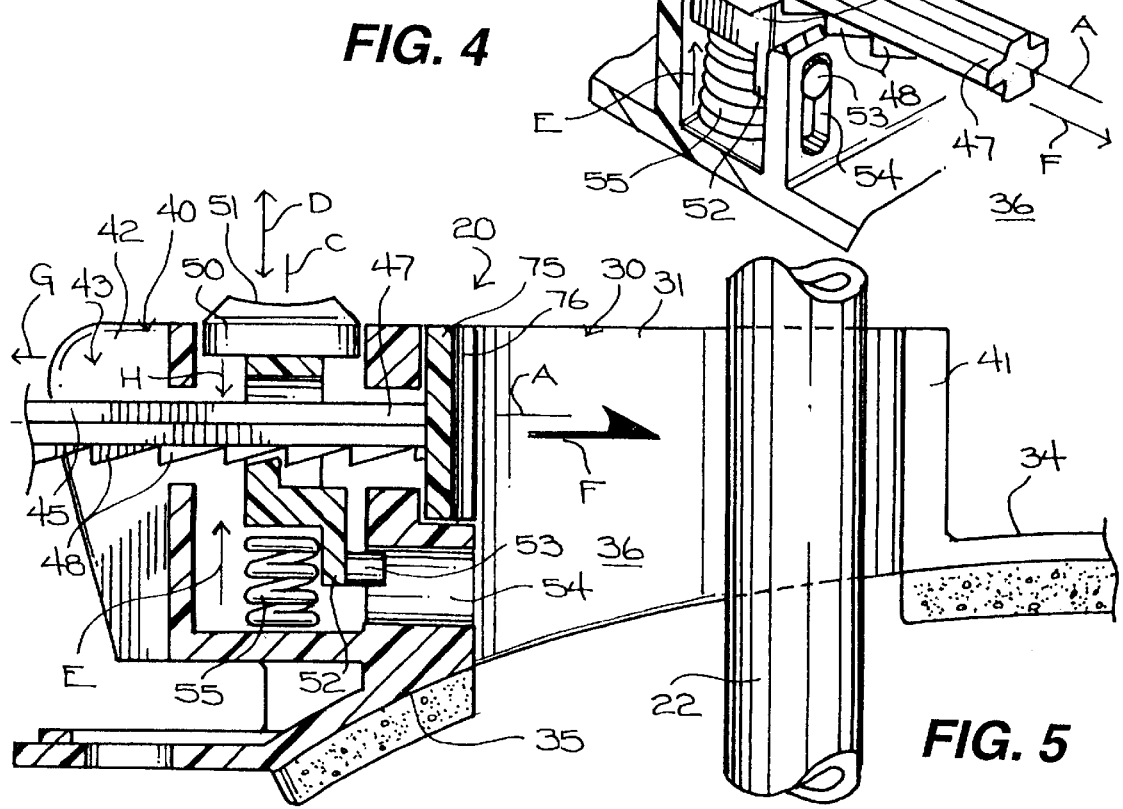

FIG. 8
FIG. 9
FIG. 10
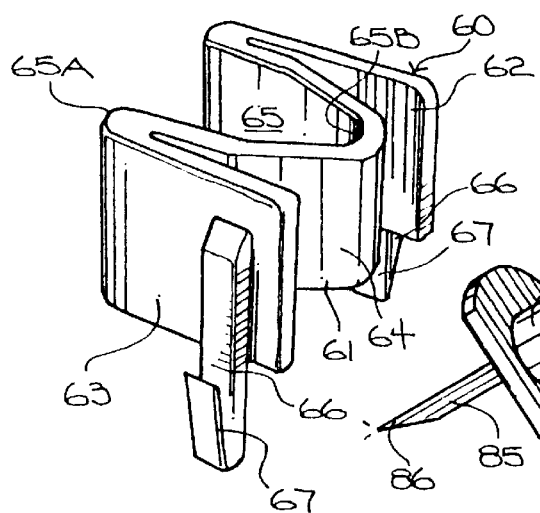
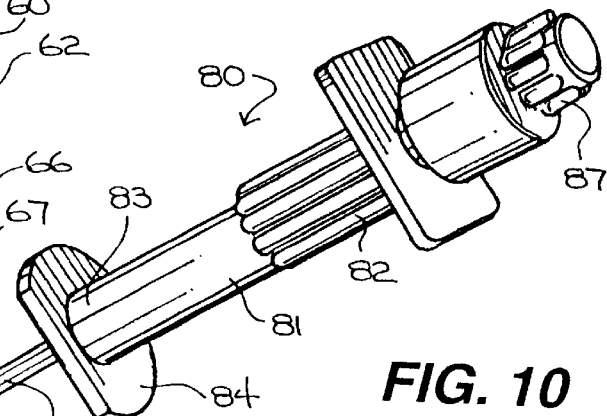
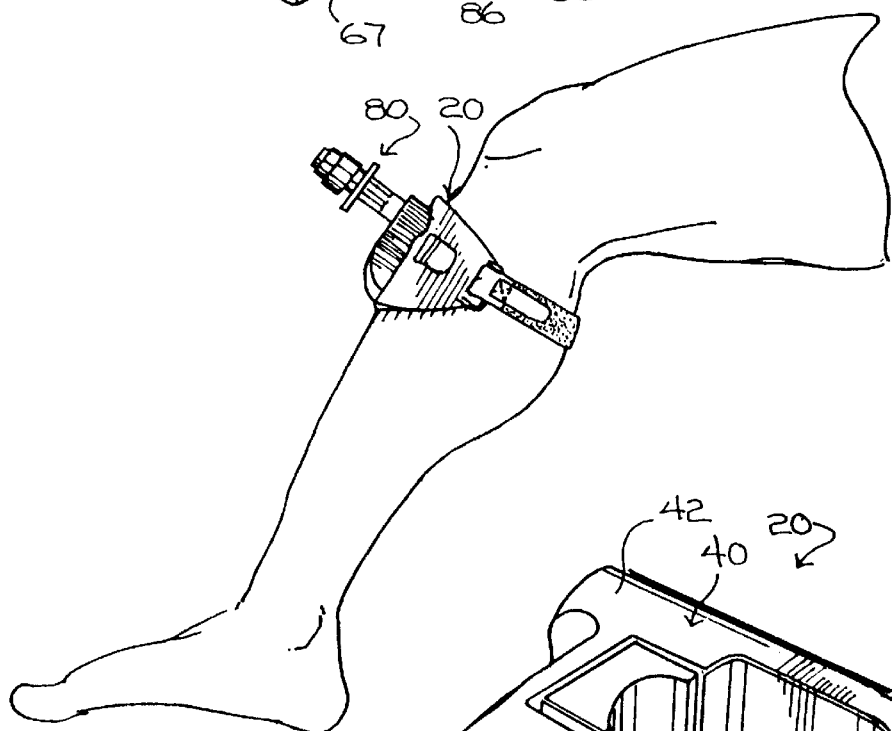
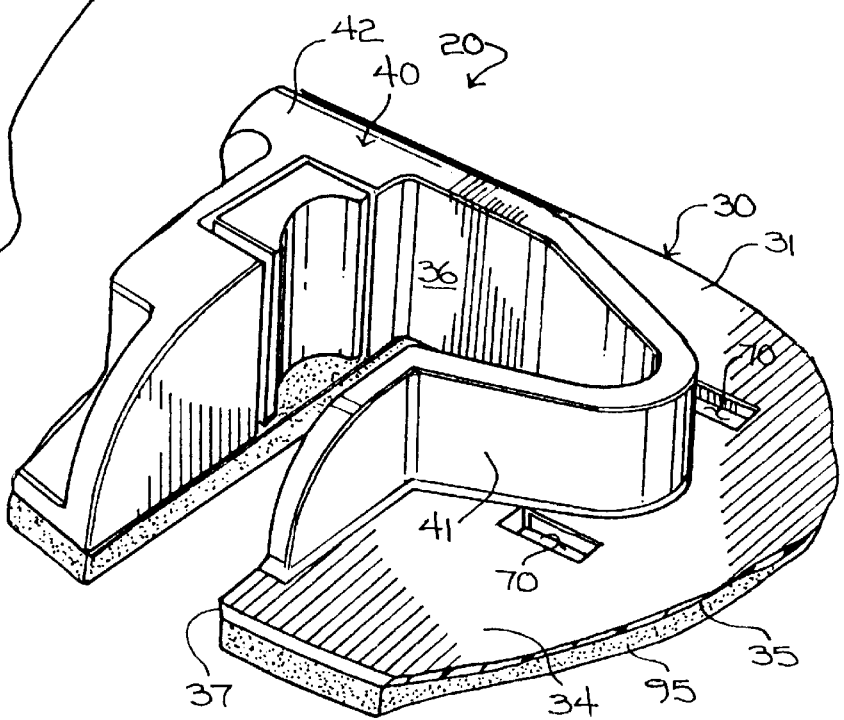
FIG. 11

COMBINATION ENDOTRACHEAL AND INTRAOSSEOUS TRANSFUSION APPARATUS HOLDER

BACKGROUND OF THE INVENTION

1. Field of the Invention

This invention relates generally to the field of medical devices.

More particularly, this invention relates to a multi-purpose medical device.

In a further and more specific aspect, the present invention relates to a combination endotracheal tube holder and interosseous transfusion apparatus holder.

2. Prior Art

Proper and efficient emergency medical care is often essential to prevent premature death, irreparable bodily injury and to ensure fast, efficient patient recovery. To this end, the prior art provides a vast array of exemplary apparatus and methods that emergency medical care technicians and doctors may use in virtually every medical emergency and non-emergency situation.

During many emergency and non-emergency medical procedures, endotracheal tubes are frequently installed into and through the mouth and trachea of the patient for communicating oxygen to the patient's lungs. To hold the endotracheal tube in place, the prior art provides an array of apparatus, commonly referred to as endotracheal tube holders, engagable with the head of the patient and the endotracheal tube for preventing the patient from removing the endotracheal tube and for preventing the endotracheal tube from becoming inadvertently dislodged.

The prior art endotracheal tube holders, although impressive, are of limited utility having no other use. In other words, the prior art endotracheal tube holders are limited by their construction for the single use of holding an endotracheal tube.

It would be highly advantageous, therefore, to remedy the foregoing and other deficiencies inherent in the prior art.

Accordingly, it is an object of the present invention to provide a multi-purpose apparatus movable from a first configuration for holding an orally routed apparatus with a patient and a second configuration for holding a non-orally routed apparatus with a patient.

Another object of the present invention is to provide a multi-purpose apparatus that is easy to construct.

And another object of the present invention is to provide a multi-purpose apparatus that is easy to use.

Still another object of the present invention is to provide a multi-purpose apparatus that easy to install.

Yet another object of the instant invention is the provision of enhancing the utility of known endotracheal tube holders.

Yet still another object of the instant invention is the provision of increasing the ease and efficiency of medical technicians and doctors to administer emergency and non-emergency care to infants, children and adults.

And a further object of the invention is to provide a multi-purpose apparatus that is inexpensive.

Still a further object of the immediate invention is to provide a multi-purpose apparatus that is safe.

Yet a further object of the invention is to provide a multi-purpose apparatus that is compact and easy to store and transport.

And still a further object of the invention is the provision of a new and improved method for holding an orally routed apparatus and for holding an interosseous transfusion apparatus with a patient.

SUMMARY OF THE INVENTION

Briefly, to achieve the desired objects of the instant invention in accordance with a preferred embodiment thereof, provided is an apparatus for holding an orally routed apparatus, such as an endotracheal tube, with a patient in a first configuration and for holding a flanged end of a body of an apparatus, such as an interosseous transfusion apparatus, with a patient in a second configuration. The apparatus is generally comprised of a base including a channel and a bite block detachably engagable with the base and having a channel substantially alignable with the channel of the base.

With the bite block engaged with the base defining a first configuration of the apparatus, the channel of the base and the channel of the bite block will substantially align to receive the orally routed apparatus. With the bite block detached from the base defining a second configuration of the apparatus, the channel of the base may receive the body having the flanged end with portions of the flanged end to overly and engage portions of the base. Provided as a means of adjustably securing the base with the patient in the first and second configurations, the present invention may further include an elastic strap having ends engagable or otherwise mounted with opposing ends of the base and operative for wrapping engagement about a patient in the first and second configurations of the apparatus.

To detachably engage the bite block with the base, provided is an engagement assembly carried by the base and a detachably engagable complemental engagement assembly carried by the bite block. In a specific example, the engagement assembly may include a plurality of spaced-apart apertures and the complemental engagement assembly may include a plurality of spaced-apart tines carried by the bite block, each one of the plurality of tines terminating with an enlarged outer end to detachably engage a one of the plurality of apertures. The tines may be provided with either an outwardly or perhaps an inwardly directed bias to urge the outer ends of the tines against portions of the base defining the apertures when installed if so desired.

The present invention may further include a means for securing the orally routed apparatus and the body of, for instance, the interosseous transfusion apparatus, with the base in the first and second configurations, respectively. In a specific example, this means for securing may be comprised of a ratchet assembly including an arm having a free end movable in reciprocal directions relative the channel of the base to engage and secure the orally routed apparatus and the body of the interosseous transfusion apparatus with the base in the first and second configurations, respectively.

Consistent with the foregoing, associated methods may also be provided.

BRIEF DESCRIPTION OF THE DRAWINGS

The foregoing and further and more specific objects and advantages of the present invention will become readily apparent to those skilled in the art from the following detailed description thereof taken in conjunction with the drawings in which:

FIG. 3 illustrates a top elevational view of the apparatus of FIG. 1;

FIG. 4 illustrates a perspective view of a ratchet assembly of the apparatus of FIG. 1, with portions of the apparatus broken away for the purposes of illustration;

FIG. 5 illustrates a vertical sectional view of the ratchet assembly set forth in FIG. 4;

FIG. 8 illustrates a perspective view of the bite block of the present invention first set forth in FIG. 6;

FIG. 9 illustrates an interosseous transfusion apparatus for use in combination with the apparatus of FIG. 1;

FIG. 10 illustrates the apparatus of FIG. 1 shown as it would appear in a second configuration as worn by a user for holding the interosseous transfusion apparatus of FIG. 9 with a patient;

FIG. 11 illustrates an enlarged fragmented perspective view of the apparatus of FIG. 1.

DETAILED DESCRIPTION OF THE PREFERRED EMBODIMENT

The present invention provides, among other things, an apparatus and method for holding an orally routed apparatus, such an endotracheal tube, with a patient in a first configuration and for holding a non-orally routed apparatus, such as an interosseous transfusion apparatus, with a patient in a second configuration. The present invention is easy to use and may be easily converted between the first and second configurations as needed.

Figure 1:
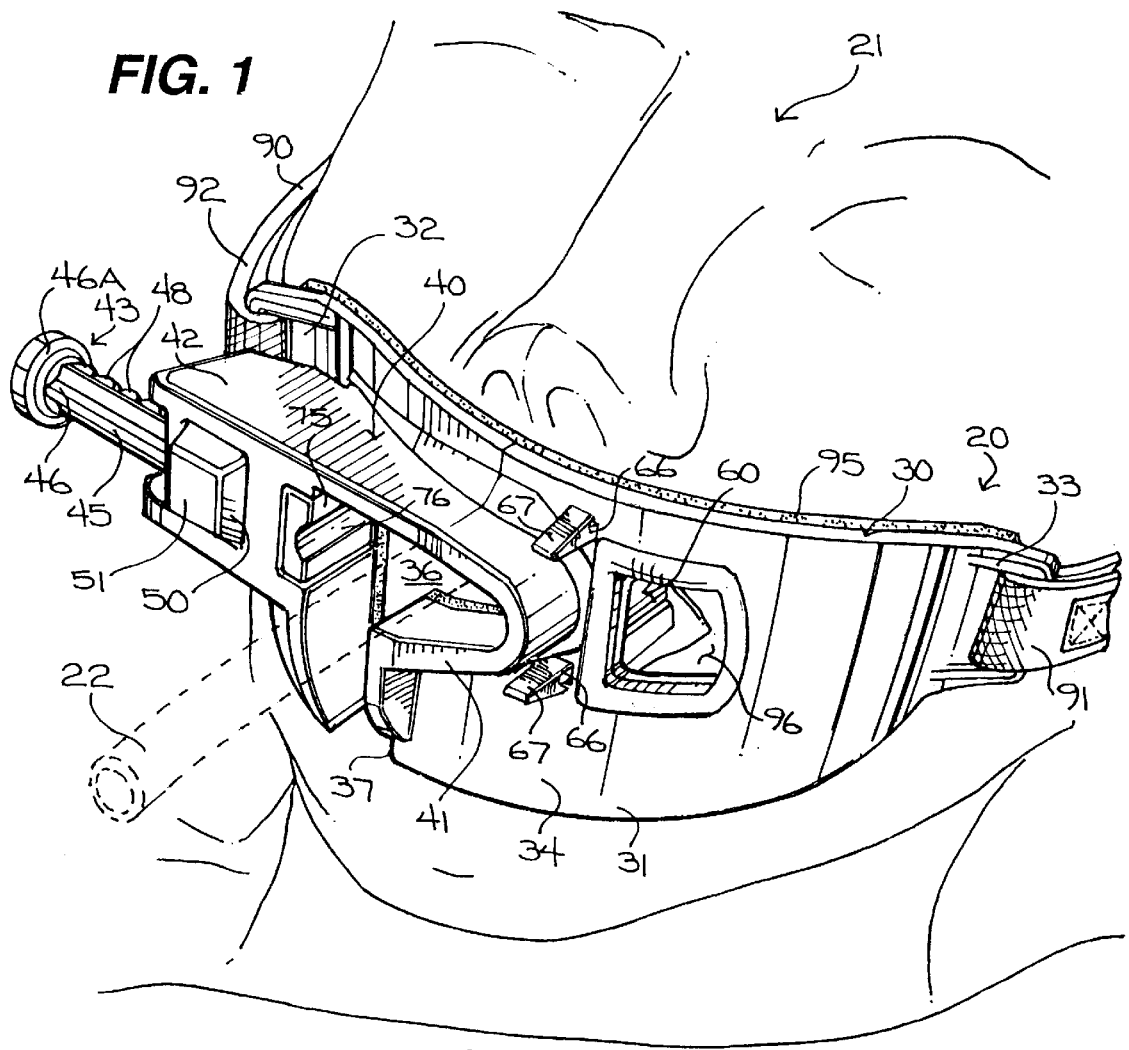
FIG. 1 illustrates an apparatus shown as it would appear in a first configuration as worn by a user for holding an orally routed apparatus.

Turning now to the drawings, in which like reference characters indicate corresponding elements throughout the several views, attention is first directed to FIG. 1 illustrating an apparatus 20 shown as it would appear in a first configuration as worn by a user or patient 21 for holding an orally routed apparatus 22 shown in the dotted outline, in accordance with a preferred embodiment of the present invention. In FIG. 1, orally routed apparatus 22 is shown as a typical endotracheal tube positioned into and through the patient's mouth and trachea in accordance with conventional practice. Although FIG. 1 illustrates orally routed apparatus 22 as an endotracheal tube, other medical apparatus that may otherwise be held into and through the mouth for any predetermined amounts of time may also be used with apparatus 20 and are intended to be included within the scope of the invention.

Figure 2:
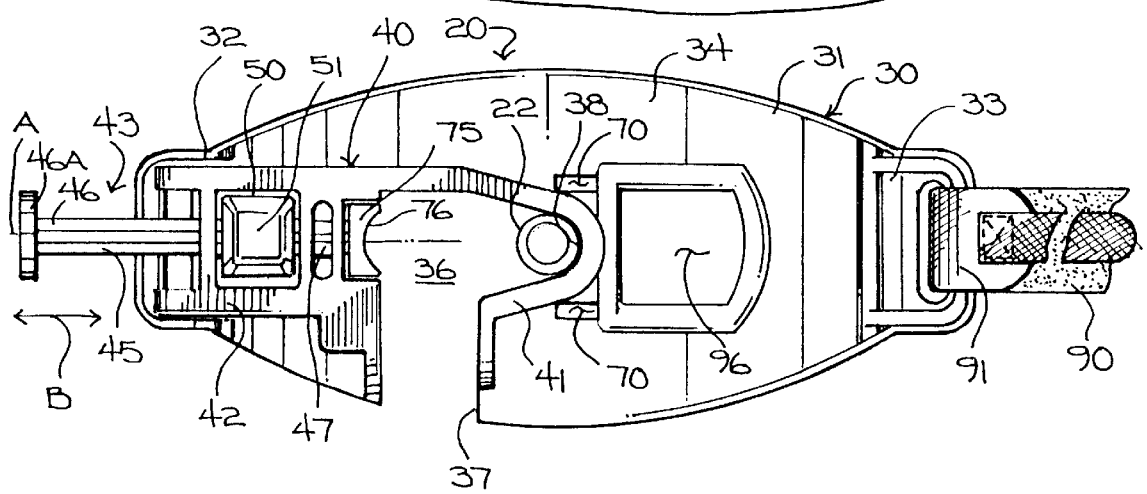
FIG. 2 illustrates a front elevational view of the apparatus of FIG. 1.

With continuing reference to FIG. 1 and additional reference to FIG. 2 illustrating a front elevational view of apparatus 20 and FIG. 3 illustrating a top elevational view of apparatus 20, apparatus 20 is generally comprised of a base 30 including an elongate and substantially arcuate member 31 having opposing free ends 32 and 33, an outer surface 34 and an inner surface 35 shown only in FIG. 3. As shown in FIGS. 1 and 2, and preferably constructed of molded plastic, polyethylene or other similarly flexible material, base 30 further includes a channel 36 having a substantially inverted L-shaped configuration, channel 36 having an open end 37 and a closed end 38 formed substantially in the shape of a V or U.

Base 30 further includes a support assembly 40 extending outwardly from outer surface 34. With continuing reference to FIGS. 1 and 2, support assembly 40 includes a sidewall 41 superimposed substantially with the perimeter of channel 36. Support assembly 40 further includes a housing 42 that carries or otherwise houses a ratchet assembly 43. As shown in FIG. 2, ratchet assembly is generally comprised of a bar or arm 45 mounted with housing 42 for movement along axis A in reciprocal directions as indicated by the double arrowed line B relative channel 36. Arm 45 is elongate and includes a first end 46 having a handle or enlargement 46A carried thereby so as to be easily grasp, a second end 47 directed toward channel 36 and, as shown in FIG. 4 illustrating a perspective view of ratchet assembly 43 and FIG. 5 illustrating a vertical sectional view of ratchet assembly 43, inclined teeth 48 carried by and extending along substantially the entire length of arm 45 from first end 46 to second end 47.

Ratchet assembly 43 still further includes pawl body 50 captured or otherwise carried by housing 42 intermediate first and second ends 46 and 47 of arm 45 for movement in reciprocal directions along axis C in the direction generally indicated by the double arrowed line D, axis C being substantially perpendicular to axis A of arm 45. In this specific example, pawl body 50 is shown as an integral member and includes an upper end 51 extending outwardly from housing 42 and a lower end 52 having a protuberance or pin 53 positioned to ride within a groove 54 formed with housing 42. Captured by housing 42 adjacent lower end 52 is a compression spring 55 operative for normally biasing pawl body 50 upwardly in the direction generally indicated by the arrowed line E for normally urging a pawl 56 carried by pawl body 50 into the interdental spaces formed between each adjacent pair of inclined teeth 48 to allow effective motion of arm 45 only in the direction generally indicated by the arrowed line F toward channel 36 of base 30. To permit movement of arm 45 away from channel 36 in the direction indicated by the arrowed line G, a user may engage upper end 51 of pawl body 50 and depress pawl body 50 downwardly in the direction indicated by the arrowed line H to overcome the bias of compression spring 55 and disengage pawl 56 from inclined teeth 48 carried by arm 45 to thus allow a user to pull arm 45 outwardly away from channel 36 as desired. Although compression spring 55 has been disclosed as a preferred means of imparting a desired bias to pawl body 50, other conventional, similar or equivalent biasing mechanisms may be used and are intended to be included within the scope of the invention.

Figure 6:
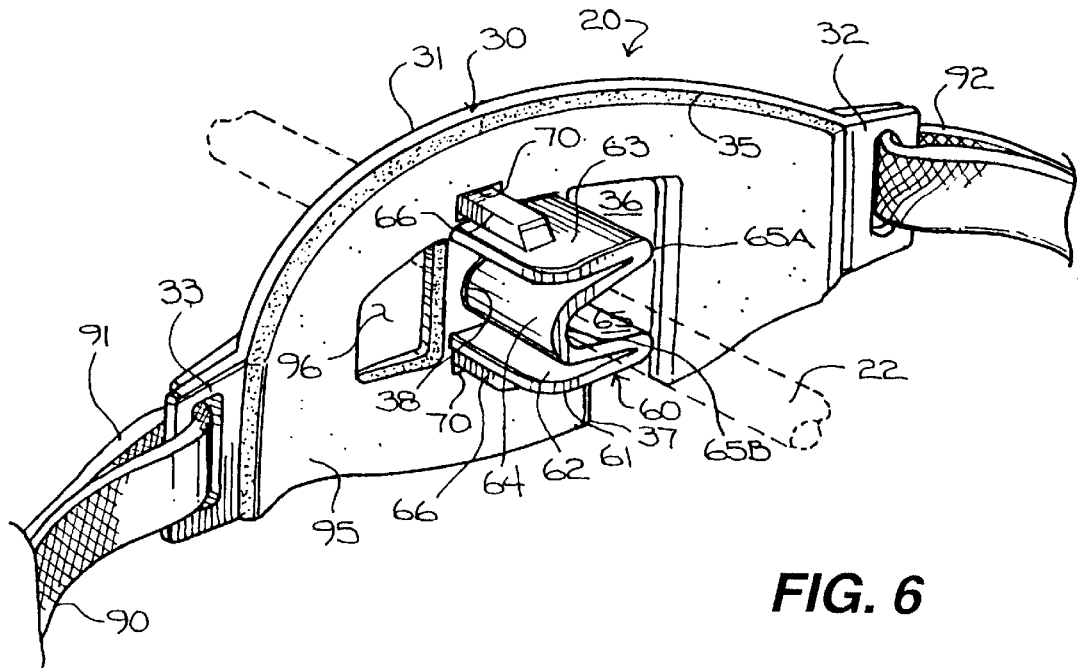
FIG. 6 illustrates a rearward perspective view of the apparatus of FIG. 1 shown as it would appear in the first configuration with a detachably engagable bite block mounted with a base of the apparatus.
Figure 7:
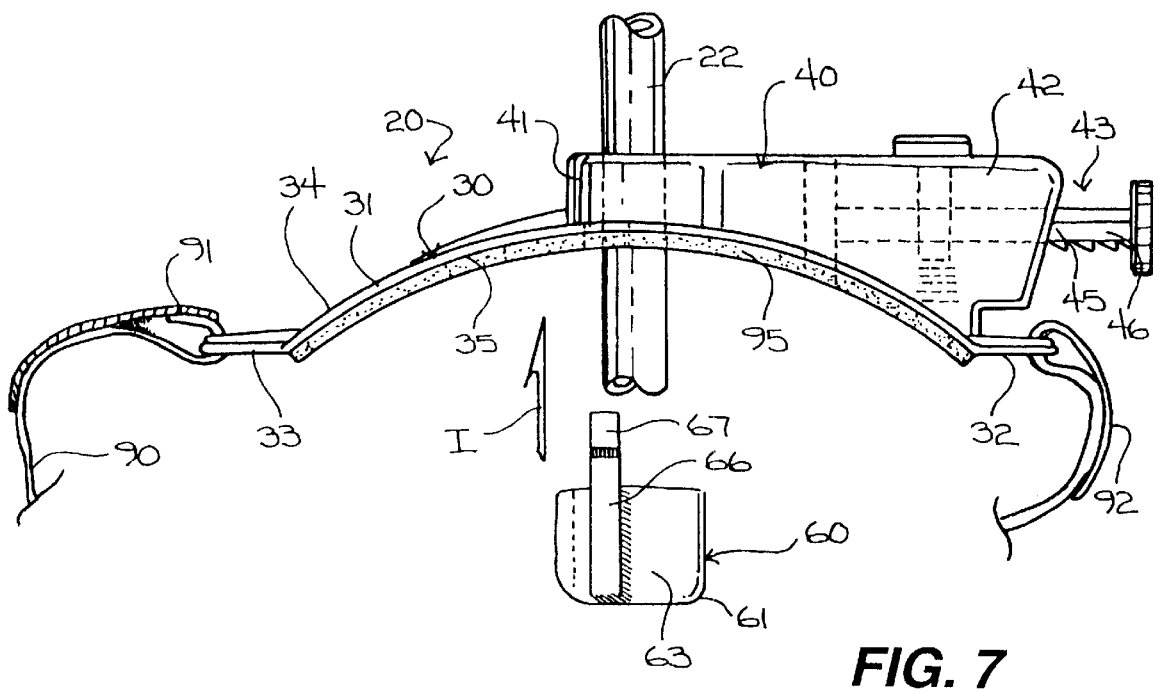
FIG. 7 illustrates a bottom elevational view of the apparatus set forth in FIG. 6 with the bite block shown as it would appear detached from the base in a second configuration of the apparatus.

Referring now to FIG. 6 and FIG. 7, the present invention further includes a bite block 60 detachably engagable with base 30 in a direction toward inner surface 35. Regarding FIG. 8 illustrating a perspective view of bite block 60, bite block 60 is preferably integrally formed and constructed of molded plastic, polyethylene or other suitably firm yet somewhat soft material and is generally comprised of a body 61 having spaced apart endwalls 62 and 63 bounding, on either side, a substantially V- or U-shaped sidewall 64 that bounds a channel 65, sidewall 64 defining an open end 65A and a closed end 65B of channel 65. Bite block 60 further includes a plurality of spaced-apart tines 66, each tine 66 being formed with and extending outwardly from each respective endwall 62 and 63. Preferably aligned in substantially parallel relation, tines 66 each terminate with an enlarged outer end 67.

With attention directed back to FIG. 7, bite block 60 is shown as it would appear detached and spaced from base 30 in a direction facing inner surface 35. With ends 67 of tines 66 directed toward inner surface 35, bite block 60 may be urged toward inner surface 35 in the direction generally indicated by the arrowed line I to insert ends 67 through apertures 70 formed through arcuate members 31 as shown in FIGS. 1 and 11 to detachably engage bite block 60 with base 30 as seen in FIGS. 1 and 6, each aperture 70 shown positioned on either side of closed end 38 of channel 36 of base 30 and spaced apart so as to substantially align with ends 67. So engaged with base 30 as shown in FIGS. 1 and 6, closed end 65B and channel 65 of bite block 60 will align substantially with closed end 38 and channel 36 of base 30. To disengage bite block 60 from base 30, a user need grasp ends 67 of tines 66, compress them inwardly together and then pull bite block 60 away from base. In a specific embodiment, tines 66 may be provided with either an outwardly divergent or perhaps an inwardly divergent bias to urge ends 67 of tines 66 against portions of base 30 defining apertures 70 when installed if so desired.

Apparatus 20 is a multi-purpose device. With bite block 60 engaged with base 30 as shown in FIG. 6 defining a first configuration of apparatus 20, apparatus 20 may be employed as a holder for an orally routed apparatus such as the endotracheal tube orally routed apparatus 22 shown in FIG. 1. In accordance with conventional practice, the endotracheal tube is generally positioned within the patient's mouth so as to be properly inserted into and through the patient's trachea. To hold the endotracheal tube in place after installation with a patient, arcuate member 31 may be positioned over a patient's face so as to directly cover the mouth, the substantially arcuate shape and flexibility of arcuate member 31 being sufficient to fit the contour of the patient's face.

Open end 37 of channel 36 receives orally routed apparatus 20, which is then positioned against closed end 38. To secure the endotracheal tube with apparatus 20, arm 45 of ratchet assembly 43 may be urged toward channel 36 in the direction generally indicated by the arrowed line F in FIG. 5 to engage the endotracheal tube and secure it against sidewall 41 thus securing the endotracheal tube with or relative channel 36 of apparatus 20. As shown in FIGS. 1, 2, 5, and 11, second end 47 of arm 45 carries an engagement element 75 having a seat or groove 76 facing channel 36. Seat 76 is formed to substantially conform to the shape of the endotracheal tube to engage and hold the endotracheal tube against sidewall 41 to prevent longitudinal and rotational movement that may be inadvertently applied to the endotracheal tube once it has been correctly positioned into and through the patient's mouth and trachea. With apparatus installed with a patient in the foregoing manner as substantially shown in FIG. 1, bite block 60 is positioned within the patient's mouth so that it can be firmly grasp by the teeth without affecting the endotracheal tube extending through channel 65.

With bite block 60 disengaged from base 30 as shown in FIG. 7 defining a second configuration of apparatus 20, apparatus 20 may be employed as a holder for, for instance, an interosseous transfusion apparatus. With momentary attention directed to FIG. 9, shown is a prior art interosseous transfusion apparatus generally designated by the reference character 80. Interosseous transfusion apparatus 80 is well known by those having regard toward the relevant art and will not be herein discussed in great detail except to an extent necessary to disclose the present invention.

In this regard, interosseous transfusion apparatus 80 is generally comprised of a tubular body 81 having a first end 82 and a second 83 having an outwardly radially extending substantially annular flange 84. Body 81 carries a hollow needle 85 extending substantially from first end 82 and terminating with a sharp outer end 86 operative for insertion into a patient in a manner to be described presently. First end 82 of body 81 carries a threaded cap 87 that may be removed for exposing the upper end (not shown) of needle 85.

Interosseous transfusion apparatus 80 is used to transfuse blood and other intravenous solutions to infant patients, juvenile patients and adult patients. Transfusing intravenous solutions to, for instance, an infant patient, especially in an emergency situation, is particularly difficult due to the inherent difficulty of finding an exposed blood vessel at the surface of the skin. Because finding an exposed blood vessel in an infant patient for normal intravenous transfusion is time consuming and often unsuccessful, intravenous transfusion to infant patients is not practical in an emergency scenario or when the life of the infant patient is at immanent risk. To transfuse intravenous solutions with interosseous transfusion apparatus 80, the medical worker may grasp interosseous transfusion apparatus 80 and plunge outer end 86 into the lower leg and into and through, for example, the femur bone for receipt within the femur bone cavity. Once installed, the medical worker may remove threaded cap 87 and couple the exposed upper end to an intravenous solution supply for transfusing or otherwise communicating the intravenous solution directly into the femur bone cavity. Those of ordinary skill will readily appreciate that the distance between flange 84 and outer end 86 of needle 85 is of an optimum extent such that with outer end 86 positioned within the femur bone cavity, flange 84 will rest against the outer surface of the leg of the patient.

Figure 12:
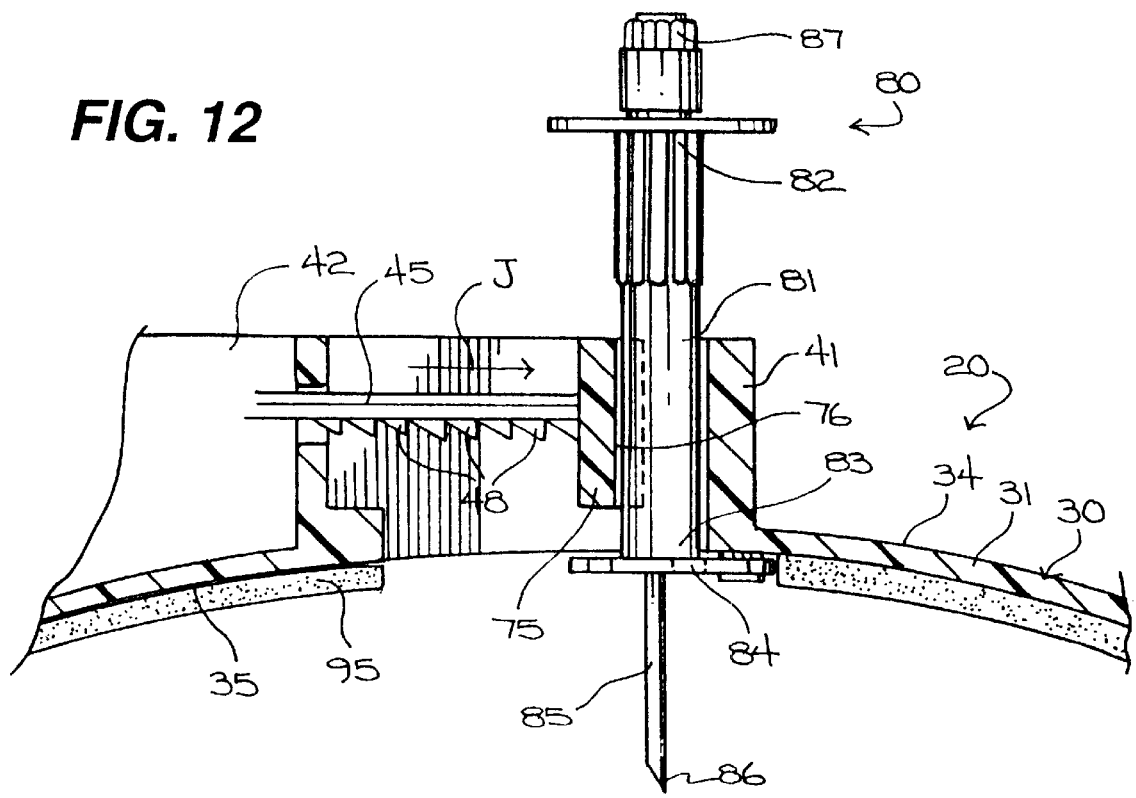
FIG. 12 illustrates a vertical sectional view of the apparatus in the second configuration as set forth in FIG. 9.

To inhibit interosseous transfusion apparatus 80 from becoming inadvertently dislodged or moved once properly installed, and in the second configuration of apparatus 20, arcuate member 31 may be positioned over a patient's leg with the substantially arcuate shape and flexibility of arcuate member 31 being sufficient to fit, or otherwise adapt to, the contour of the patient's leg. Arcuate member 31 may be further positioned upon the patient's leg with open end 37 of channel 36 to receive the interosseous transfusion apparatus 80 which is then positioned, with proper movement of arcuate member 31, against closed end 38 to reside against and substantially parallel with tubular body 81 as shown substantially in FIG. 12 with portions of flange 84 to overly and engage portions of inner surface 35 of arcuate member 31 at a point substantially underlying sidewall 41. To secure interosseous transfusion apparatus 80 with apparatus 20, arm 45 of ratchet assembly 43 may be urged toward channel 36 in the direction generally indicated by the arrowed line J in FIG. 12 to engage seat 76 of engagement element 76 against tubular body 81 and secure it against sidewall 41 thus securing the interosseous transfusion apparatus 80 with channel 36 of apparatus 20.

To adjustably secure base 30 of apparatus 20 with a patient in the first and second configurations, and with attention directed back to FIG. 3, the present invention further includes an elastic strap 90 having ends 91 and 92 mounted with arcuate member 31 at free ends 32 and 33. Each end 91 and 92 of elastic strap 90 is formed so as to form a loop to engage the free ends 32 and 33 of arcuate member 31. Furthermore, each end 91 and 92 may, in a specific example, further include a hook and loop engagement mechanism, such as provided under the exemplary trademark VELCRO®, to facilitate the adjustable and detachable engagement of ends 91 and 92 with arcuate member 31. In this regard, elastic strap 90 is operative for wrapping engagement about the head of a patient in the first configuration of apparatus 20 as shown in FIG. 1 for holding orally routed apparatus 22, and for wrapping engagement about a leg of a patient in the second configuration of apparatus 20 as shown in FIG. 10 for holding interosseous transfusion apparatus 80.

Elastic strap 90 is an important feature of the present invention as it provides an exemplary means for adjustably securing base 30 with a patient both in the first and second configurations of apparatus 20. In this regard, elastic strap 90 operates to compress and secure inner surface 35 of arcuate member 31 against the face of a patient in the first configuration of apparatus 20 and against the outer surface of the leg of a patient in the second configuration of apparatus 20. This feature is especially important during use of apparatus 20 in the second configuration for securing interosseous transfusion apparatus 80 with a patient in that elastic strap 90 operates to compress portions of inner surface 35 of arcuate member 31 substantially underlying sidewall 41 against portions of flange 84 for correspondingly compressing and holding flange 84 against the leg of the patient. This, in combination with ratchet assembly 43, provides for securement and immobilization of interosseous transfusion apparatus 80 with the leg of the patient for inhibiting inadvertent movement or dislodgment of interosseous transfusion apparatus 80 after installation with a patient. Although elastic strap 90 has been disclosed as a preferred mechanism for securing base 30 with a patient in the first and second configurations of apparatus, other similar engagement mechanisms may also be used and are intended to be included within the scope of the invention.

As shown in FIGS. 1, 3, 6, 7, 11 and 12, the present invention may further include a foam pad carried by or otherwise mounted with inner surface 35 of arcuate member 31 for providing comfort against a patient when installed. Furthermore, it should be noted the arcuate member 31 is provided with an access opening 96 (shown in FIGS. 1, 2, and 6) for permitting various medical instruments to be passed therethrough so as to be, for instance, inserted into the mouth of a patient in the first configuration of apparatus 20 or engaged with the leg of a patient in the second configuration of apparatus 20, as may be necessary.

The present invention has been described above with reference to a preferred embodiment. However, those skilled in the art will recognize that changes and modifications may be made in the described embodiments without departing from the nature and scope of the present invention. For instance, although apertures 70 and tines 66 have been disclosed as a preferred engagement assembly and complemental engagement assembly, respectively, for facilitating the detachable engagement of bite block 60 with base 30, other suitable engagement mechanisms may also be used. As an example, bite block 60 and or base 30 may be provided with an adhesive element, if so desired, for facilitating adhesive engagement of bite block 60 with base 30 if so desired. Furthermore, apparatus 20 may also be used for securing a tubular apparatus installed with a patient to extending into and through an incision formed through the neck and into trachea for communicating, for instance, oxygen to a patient. The procedure for installing a tubular apparatus into and through the trachea through an incision formed through the neck of a patient is commonly referred to as a cricothyroidotomy. In this regard, apparatus 20, in the second configuration, may be installed to hold such a tubular apparatus as desired as one installed in by virtue of a cricothyroidotomy. In this regard, elastic strap 90 would, of course, wrap about the neck of the patient for securing base 30 with the patient.

Various and further changes and modifications to the present invention herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. An apparatus for holding an orally routed apparatus and for holding a flanged end of a body, the apparatus comprising:

a base including a channel;

a bite block detachably engagable with the base and having a channel substantially alignable with the channel of the base;

with the bite block engaged with the base defining a first configuration of the apparatus, the channel of the base and the channel of the bite block to substantially align and receive the orally routed apparatus;

with the bite block detached from the base defining a second configuration of the apparatus, the channel of the base to receive a body having a flanged end with portions of the flanged end to overly and engage portions of the base; and means for securing the orally routed apparatus and the body with the base in the first and second configurations, respectively.

2. The apparatus of claim 1, further including means for adjustably mounting the base with a patient.

3. The apparatus of claim 2, wherein the means for adjustably mounting the base with the patient is comprised of an elastic strap having ends mounted with the base at opposing ends thereof.

4. The apparatus of claim 1, further including means for detachably engaging the bite block with the base.

5. The apparatus of claim 4, wherein the means for detachably engaging the bite block with the base is comprised of:

an engagement assembly carried by the base; and a detachably engagable complemental engagement assembly carried by the bite block.

6. The apparatus of claim 5, wherein the engagement assembly includes a plurality of spaced-apart apertures.

7. The apparatus of claim 6, wherein the complemental engagement assembly includes a plurality of spaced-apart tines carried by the bite block, each one of the plurality of tines terminating with an enlarged free end to detachably engage a one of the plurality of apertures in the second configuration.

8. The apparatus of claim 1, wherein the means for securing the orally routed apparatus and the body with the base in the first and second configurations, respectively, comprises a ratchet arm having a free end movable in reciprocal directions relative the channel of the base.

9. The assembly of claim 1, wherein the base further includes an access opening to allow free access to a patient's mouth in the first configuration.

10. A method for holding an orally routed apparatus and for holding a flanged end of a body, the method comprising the steps of:

providing a base including a channel;

providing a bite block detachably engagable with the base and having a channel substantially alignable with the channel of the base;

with the bite block engaged with the base defining a first configuration of the apparatus, positioning an orally routed apparatus in the channel of the base and the channel of the bite block;

with the bite block detached from the base defining a second configuration of the apparatus, positioning a body having a flanged end in the channel of the base with portions of the flanged end to overly portions of the base; and securing the orally routed apparatus and the body with the base in the first and second configurations, respectively.

11. The method of claim 1, further including the step of adjustably mounting the base with a patient in the first and second configurations.

12. The method of claim 11, wherein the step of adjustably mounting the base with the patient further includes the step of providing an elastic strap having ends mounted with the base at opposing ends thereof.

13. The method of claim 10, further including the step of providing a means for detachably engaging the bite block with the base.

14. The method of claim 13, wherein the step of providing a means for detachably engaging the bite block with the base further includes the steps of:

providing an engagement assembly carried by the base; and providing a detachably engagable complemental engagement assembly carried by the bite block.

15. The method of claim 14, wherein the step of providing an engagement assembly further includes the step of providing a plurality of spaced-apart apertures.

16. The method of claim 15, wherein the step of providing a complemental engagement assembly further includes the step of providing a plurality of spaced-apart tines carried by the bite block, each one of the plurality of tines terminating with an enlarged free end to detachably engage a one of the plurality of apertures in the second configuration.

17. The method of claim 10, wherein the step of securing the orally routed apparatus and the body with the base in the first and second configurations, respectively, further includes the step of providing a ratchet arm having a free end movable in reciprocal directions relative the channel of the base.

* * * * *